United States Patent [19]
Ravikumar et al.

[11] Patent Number: 6,084,082
[45] Date of Patent: Jul. 4, 2000

[54] LACTAM NUCLEIC ACIDS

[75] Inventors: Vasulinga Ravikumar; Venkatraman Mohan, both of Carlsbad, Calif.

[73] Assignee: Isis Pharmaceuticals, Inc., Carlsbad, Calif.

[21] Appl. No.: 09/173,212

[22] Filed: Oct. 15, 1998

Related U.S. Application Data

[62] Division of application No. 08/684,423, Jul. 19, 1996, Pat. No. 5,866,691, which is a division of application No. 08/243,368, May 16, 1994, Pat. No. 5,554,746.

[51] Int. Cl.$^7$ .......................... C07H 19/00; C07H 21/02; C12Q 1/68; A01N 43/04
[52] U.S. Cl. .............................. 536/22.1; 435/6; 514/44; 536/23.1; 536/25.3; 536/25.31; 536/25.33; 536/25.34
[58] Field of Search .................................. 435/6; 514/44; 536/22.1, 23.1, 25.3, 25.31, 25.33, 25.34

[56] References Cited

U.S. PATENT DOCUMENTS

| | | | |
|---|---|---|---|
| 4,458,066 | 7/1984 | Caruthers et al. | 536/27 |
| 4,500,707 | 2/1985 | Caruthers et al. | 536/27 |
| 5,132,418 | 7/1992 | Caruthers et al. | 536/27 |
| 5,210,264 | 5/1993 | Yau | 558/167 |

OTHER PUBLICATIONS

Stec, Wojciech J. et al., "Bis(O,O–Diisopropoxy Phosphinothioyl) Disulfide—A Highly Efficient Sulfurizing Reagent for Cost–Effective Synthesis of Oligo (Nucleoside Phosphorothioate)s", *Tetrahedron Letters*, vol. 34, No. 33, pp. 5317–5320, 1993.

Horn, Thomas et al., "A Chemical 5'–Phosphorylation of Oligodeoxyribonucleotides That Can Be Monitored by Trityl Cation Release", *Tetrahedron Letters*, vol. 27, No. 39, pp. 4705–4708, 1986.

Thuong, Nguyen T. et al., "Synthese Et Reactivite D'oligothymidylates Substitues Par Un Agent Intercalant Et Un Groupe Thiophosphate", *Tetrahedron Letters*, vol. 28, No. 36, pp. 4157–4160, 1987.

Kamer, P.C.J. et al., "An Efficient Approach Toward The Synthesis of Phosphorothioate Diesters Via The Schonberg Reaction", *Tetrahedron Letters*, vol. 30, No. 48, pp. 6757–6760, 1989.

Rao, M. Vaman et al., "Dibenzoyl Tetrasulphide—A Rapid Sulphur Transfer Agent in the Synthesis of Phosphorothioate Analogues of Oligonucleotides", *Tetrahedron Letters*, vol. 33, No. 33, pp. 4839–4842, 1992.

Vu, Huynh et al., "Internucleotide Phosphite Sulfurization With Tetraethylthiuram Disulfide. Phosphorothioate Oligonucleotide Synthesis Via Phosphoramidite Chemistry". *Tetrahedron Letters*, vol. 32, No. 26, pp. 3005–3008, 1991.

Beaucage, Serge L. et al., "Advances in the Synthesis of Oligonucleotides by the Phosphoramidite Approach", *Tetrahedron*, vol. 48, No. 12, pp. 2223–2311, 1992.

Iyer, Radhakrishnan P. et al., "3H–1,2–Benzodithiole–3–one 1,1–Dioxide as an Improved Sulfurizing Reagent in the Solid–Phase Synthesis of Oligdeoxyribonucleoside Phosphorothioates", *J. Am. Chem. Soc.*, 112, 1253–1254, 1990.

Iyer, Radhakrishnan P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 55, 4693–4699, 1990.

Damha, Masad J. et al., "An Improved Procedure for Derivatization of Controlled–pore Glass Beads For Solid–Phase Oligonucleotide Synthesis", *Nucleic Acids Research*, vol. 18. No. 13, 3813–3821, 1990.

Agrawal, S., "Protocols For Oligonucleotides And Analogs", *Humana Press*, Totowa NJ 1993.

Green et al., "Protective Groups In Organic Synthesis", 2d Edition, John Wiley & Sons, NY 1991.

Gait, M.J. "Oligonucleotide Synthesis, A Practical Approach", Ed. IL: New York, 1984, Chapter 1.

F. Eckstein, "Oligonucleotides And Analogs: A Practical Approach", *IRL Press*, 88–91.

*Primary Examiner*—Jezia Riley
*Attorney, Agent, or Firm*—Woodcock Washburn Kurtz Mackiewicz & Norris LLP

[57] ABSTRACT

Novel β-lactam monomers bearing various functional groups are prepared. The novel β-lactam monomers can be joined into oligomeric compounds such as via preferred phosphate linkages including phosphodiester and phosphorothioate linkages. Useful functional groups include nucleobases as well as polar groups, hydrophobic groups, ionic groups, aromatic groups and/or groups that participate in hydrogen bonding. The oligomeric compounds are useful as diagnostic and research reagents.

14 Claims, No Drawings

LACTAM NUCLEIC ACIDS

This Application is a division of U.S. Application Ser. No. 08/684,423 filed Jul. 19, 1996, now U.S. Pat. No. 5,886,691, which is a division of U.S. Application Ser. No. 08/243,368, filed May 16, 1994, now U.S. Pat. No. 5,554,746, the disclosures of which are hereby incorporated by reference in their entireties.

BACKGROUND OF THE INVENTION

1. Field of the Invention

The present invention is directed to a new class of polymeric compounds for binding to complementary DNA and RNA strands. In particular, the invention concerns compounds wherein naturally-occurring nucleobases or other nucleobase-binding moieties are covalently bound to an oligolactamtide, i.e., a backbone comprising repeating units that are phosphoric acid esters of β-lactams. These compounds are useful for diagnostics, research reagents and therapeutics. The present invention is also directed to processes for synthesizing such compounds, and to intermediates used in such processes.

The ultimate mechanism of action for most conventional therapeutic agents, i.e. drugs, is by way of modulation of one or more targeted endogenous proteins, e.g., enzymes. Such agents, however, typically lack total specificity for their target proteins, and instead interact with other proteins as well. Thus, a relatively large dose of the agent must be used to effectively modulate a target protein; and the agent can cause undesired side effects as the result of interference in the action of the non-target proteins. Typical daily doses of such conventional agents are from $10^{-5}$–$10^{-1}$ millimoles per kilogram of body weight or $10^{-3}$–10 millimoles for a 100 kilogram person. If this modulation instead could be effected by interaction with or inactivation at a point in the biological pathway at an earlier stage, a dramatic reduction in the necessary amount of the therapeutic agent necessary could likely be achieved, along with a corresponding reduction in side effects. Further reductions could be effected if such interaction could be rendered site-specific.

Proteins are produced in biological systems ultimately from genes that encode them. A gene performs its basic function by transcription of its encoded information to messenger RNA (mRNA) which, by interaction with the ribosomal complex in a synthetic process called translation, directs the assembly of the protein coded for by its sequence. Translation requires the presence of various co-factors and the amino acid building blocks for the protein, and their transfer RNAs (tRNA), all of which are present in normal cells.

In order for transcription to be initiated, there must be recognition of a specific promoter DNA sequence by the RNA-synthesizing enzyme, RNA polymerase. In many cases in prokaryotic cells, and probably in all cases in eukaryotic cells, this recognition is preceded by sequence-specific binding of a protein transcription factor to the promoter. Other proteins which bind to the promoter, but whose binding prohibits action of RNA polymerase, are known as repressors. Thus, gene activation typically is regulated positively by transcription factors and negatively by repressors. These genetic regulatory mechanisms and the ability to influence them have significant implications for diagnostics and therapeutics. Since a functioning gene continually produces mRNA, it is advantageous if gene transcription is modulated or blocked totally.

Oligonucleotides have been shown to interact with mRNA and other components associated with gene transcription. By virtue of such interaction, synthetic preparations of naturally occurring oligonucleotides and synthetic oligonucleotide derivatives and analogs which do not occur in nature, have become valuable tools for research and important agents in diagnostic, therapeutic and other applications. Increasingly, there is a demand for such improved oligonucleotides, oligonucleotide analogs, as well as for methods for their preparation.

Oligonucleotides have been used in a number of areas of research. In genomic research oligonucleotides have been used as probes and primers. Oligonucleotides are also useful in devising diagnostics since they can specifically hybridize to nucleic acids of interest in the etiology of a given disease. Oligonucleotides are also being tested as therapeutic moieties in the treatment of disease states in animals and man. For example, workers in the field have now identified oligonucleotide therapeutic compositions that are capable of modulating expression of genes implicated in viral, fungal and metabolic diseases. It has now become routine to synthesize oligodeoxyribonucleotides and oligoribonucleotides having hundreds of base pairs (bp) by solid phase methods using commercially available, fully automatic synthesis machines. In short, oligonucleotides are important molecules having a large commercial impact in biotechnology and medicine. As a consequence, improved oligonucleotides and methods for the synthesis of improved oligonucleotides, which afford reduced cost and environmental impact, along with increased efficiency and convenience, are also in demand.

Unmodified oligonucleotides, i.e. natural phosphodiester linked oligonucleotides, are unpractical for many uses because they have short in vivo half-lives or they suffer from a limited ability to penetrate cell membranes. In order to improve half life as well as membrane penetration, a large number of variations in polynucleotide backbones have been undertaken. These variations include the use of methylphosphonates, monothiophosphates, dithiophosphates, phosphoramidates, phosphate esters, bridged phosphoramidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAS, α-anomeric bridges, and borane derivatives. These analogues have various properties. Only a few have proved to have such a combination of properties that render them substitutes for natural oligonucleotides.

One of the most useful oligonucleotide analogues discovered to date is a class of compounds known as peptide nucleic acids. These compounds have been found to have enhanced hybridization to complimentary DNA and RNA strands as compared to most other known oligonucleotide analogues as well as nuclease and protease stability. Peptide nucleic acids have neutral, amide linked backbones. Retention of a phosphorous atom in oligomeric backbones is considered to be highly desirable for certain utilities since such backbones are capable of providing a charged species and for providing a potential site for interactions with peptides, as for instance with transcription factors.

The β-lactam nucleic acid oligomers of the present invention are expected to exhibit superior properties as compared to prior reagents in that they mimic the higher affinity for complementary single stranded DNA (ssDNA) exhibited by peptide nucleic acids but, unlike peptide nucleic acids, the β-lactam backbone is phosphorous linked resulting in a charged compound. The β-lactam compounds are also expected to form triple helices where a first β-lactam nucleic acid strand binds with RNA or ssDNA and a second β-lactam nucleic acid strand binds with the resulting double helix or with the first β-lactam nucleic acid strand. β-lactam nucleic acids are generally water soluble to facilitate both diagnostic and research reagent use as well as cellular uptake. Moreover, β-lactam nucleic acids contain the β-lactam structure. Such structure is expected to make them biostable and resistant to enzymatic degradation, for example, by proteases.

With regard to the novel methods of preparation for the β-lactam nucleic acids of the present invention, it is noted that methods have been employed heretofore for preparing oligonucleotides that utilize solid-phase synthesis wherein an oligonucleotide is prepared on a polymer or other solid support. Such solid-phase synthesis relies on sequential addition of nucleotides to one end of a growing oligonucleotide. Typically, a first nucleoside is attached to an appropriate support, e.g. long chain alkyl amine controlled pore glass (LCAA CPG), and nucleotide precursors are added stepwise to elongate the growing oligonucleotide. The nucleotide precursors are conventionally reacted with the growing oligonucleotide using the principles of a "fluidized bed" for mixing of the reagents, where solid supports composed of silica are used. While some of the techniques of such conventional processes are used in the novel methods of the present invention, nowhere is there a suggestion of the novel reactants and steps that characterize the present methods.

OBJECTS OF THE INVENTION

It is an object of this invention to provide novel monomeric β-lactamsides and β-lactamtides.

It is another object of the invention to provide novel oligomeric β-lactamtides.

It is a further object of the invention to provide methods for preparing and using oligomeric β-lactamtides.

SUMMARY OF THE INVENTION

Compounds of the invention may include oligomeric compounds of Structure I:

ing the pharmacodynamic properties of an oligolactamtide, or a reporter ligand;

$A_l$ and each $A_m$, independently are $(CR_6R_7)_x$ where $R_6$ and $R_7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR_3R_4$ and $SR_5$, where each of $R_3$ and $R_4$ is independently selected from the group consisting of hydrogen, $(C_1-C_4)$alkyl, alkoxy, or alkylthio-substituted $(C_1-C_4)$ alkyl, alkoxy, alkylthio and amino; and $R_5$ is hydrogen, $(C_1-C_6)$alkyl, hydroxy-, alkoxy-, or alkylthio- substituted $(C_1-C_6)$alkyl, or $R_6$ and $R_7$ taken together complete an alicyclic system;

$E_1$ and $E_2$, independently, are H, a hydroxyl protecting group, an activated solid support, a conjugate group, a reporter group, a polyethylene glycol, an alkyl, an oligonucleotide, a phosphate, a phosphite, an activated phosphate, or an activated phosphite;

Z is OH, SH, $CH_3$, or $NR_1R_2$;

$R_1$ and each $R_2$, independently, are H, $C_2-C_{10}$ alkyl, $C_2-C_{10}$ alkenyl, $C_2-C_{10}$ alkynyl, $C_4-C_7$ carbocylo alkyl or alkenyl, a heterocycle, an ether having 2 to 10 carbon atoms and 1 to 4 oxygen or sulfur atoms, a polyalkyl glycol, or $C_7-C_{14}$ aralkyl;

Y is oxygen or sulfur;

n is an integer from 1 to 60;

$e_1$ and each $e_m$, independently are 0 or an integer from 1 to 6;

$b_1$ and each $b_m$, independently are 0 or an integer from 1 to 6;

In certain preferred embodiments, $B_l$ and each $B_m$ are independently selected as naturally occurring nucleobases. In further preferred embodiments $B_l$ and each $B_m$ are independently selected as non naturally occurring nucleobases. In yet other preferred embodiments $e_l$, $e_m$, $b_l$, and each $b_m$ are, independently, an integer from 1 to about 4.

In preferred embodiments of the invention n is from 1 to about 40. A more preferred range of n is from 1 to about 20.

Compounds of the invention may also include monomeric compounds of Structure II:

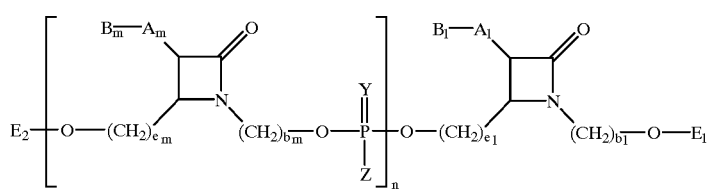

I wherein $B_l$ and each $B_m$, independently are a naturally occurring nucleobase, a non-naturally occurring nucleobase, a DNA intercalator, a nucleobase-binding group, hydrogen, hydroxyl, a $(C_1-C_4)$ alkanoyl, an aromatic moiety, or a heterocyclic moiety, which may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $N_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligolactamtide, a group for improv-

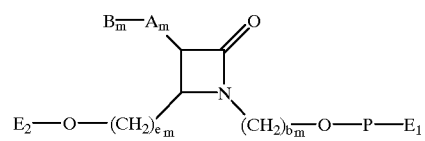

II wherein $B_m$ is a naturally occurring nucleobase, a non-naturally occurring nucleobase, a DNA intercalator, a nucleobase-binding group, hydrogen, hydroxyl, a $(C_1-C_4)$ alkanoyl, an aromatic moiety, or a heterocyclic moiety, which may be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligolactamtide, a group for improving the pharmacodynamic properties of an oligolactamtide, or a reporter ligand;

$A_1$ is $(CR_6R_7)_x$ where $R_6$ and $R_7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR_3R_4$ and $SR_5$, where each of $R_3$ and $R_4$ is independently selected from the group consisting of hydrogen, $(C_1-C_4)$alkyl, alkoxy, or alkylthio-substituted $(C_1-C_4)$ alkyl, alkoxy, alkylthio and amino; and $R_5$ is hydrogen, $(C_1-C_6)$alkyl, hydroxy-, alkoxy-, or alkylthio-substituted $(C_1-C_6)$ alkyl, or $R_6$ and $R_7$ taken together complete an alicyclic system;

X is an integer from 1 to 10, and can be 0 only when $B_m$ is not hydrogen or hydroxyl;

E1 and E2, independently, are H, a hydroxyl protecting group, an activated solid support, a conjugate group, a reporter group, a polyethylene glycol, an alkyl, an oligonucleotide, a phosphate, a phosphite, an activated phosphate, or an activated phosphite;

$e_m$ is 0 or an integer from 1 to 6;

$b_m$ is 0 or an integer from 1 to 6;

In certain preferred embodiments, $B_m$ is selected as a naturally occurring or non naturally occurring nucleobase.

In other preferred embodiments $e_m$ and $b_m$ are independently an integer from 1 to about 4.

Further in accordance with this invention there are provided methods for preparing β-lactamtides that include the steps of:

Providing a β-lactam having a functional group, a protected hydroxyl group, and a hydroxyl group covalently bonded thereto. The functional group is a naturally occurring nucleobase, a non-naturally occurring nucleobase, a DNA intercalator, a nucleobase-binding group, hydrogen, hydroxyl, a $(C_1-C_4)$alkanoyl, an aromatic moiety, or a heterocyclic moiety, furthermore, said functional group can be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligolactamtide, a group for improving the pharmacodynamic properties of an oligolactamtide, or a reporter ligand. Attaching the β-lactam to a solid support via the hydroxyl group. Treating the protected hydroxyl group with a deprotecting reagent to give a free hydroxyl group. Reacting the free hydroxyl group with a β-lactamtide having an activated phosphite group, a functional group as defined above, and a protected hydroxyl group thereon to form a phosphite triester. Oxidizing the phosphite triester to a phosphate triester.

Repetition of the above steps of deprotecting the protected hydroxyl and treating with a β-lactamtide adds a further β-lactamtide phosphite triester unit. Oxidation of the resulting β-lactamtide phosphite triester unit will give the phosphate triester. This iterative process thus increases the length of the oligomer.

In certain embodiments of the invention the functional group attached to the β-lactam and the functional group attached to the β-lactamtide is attached using a tether. The tether is selected from $(CR_6R_7)_x$ where $R_6$ and $R_7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR_3R_4$ and $SR_5$, where each of $R_3$ and $R_4$ is independently selected from the group consisting of hydrogen, $(C_1-C_4)$ alkyl, alkoxy, or alkylthio-substituted $(C_1-C_4)$alkyl, alkoxy, alkylthio and amino; and $R_5$ is hydrogen, $(C_1-C_6)$alkyl, hydroxy-, alkoxy-, or alkylthio-substituted $(C_1-C_6)$alkyl, or $R_6$ and $R_7$ taken together complete an alicyclic system, and where $x$ is an integer from 1 to 10, and can be 0 only when said functional group is not hydrogen or hydroxyl. In other embodiments of the invention the hydroxyl group and the protected hydroxyl group attached to the β-lactam and the protected hydroxyl group and the activated phosphite group attached to the β-lactamtide are attached using a $C_1$ to about $C_6$ alkyl tether. A more preferred length of the alkyl tether is $C_1$ to $C_3$ alkyl tether.

In certain further embodiments of the invention the β-lactam is substituted with the hydroxyl group covalently bonded to the N-1 position and the protected hydroxyl covalently bonded to the C-4 position. In other embodiments the hydroxyl group is covalently bonded to the N-1 position and the protected hydroxyl group is covalently bonded to the C-4 position are bound via tethers that are from $C_1$, to about $C_3$ alkyl. In certain further embodiments of the invention the β-lactamtide is substituted with the protected hydroxyl group covalently bonded to the C-4 position and the activated phosphite group covalently bonded to the N-1 position. In other embodiments the protected hydroxyl group covalently bonded to the C-4 position and the protected hydroxyl group covalently bonded to the N-1 position are bound via tethers that are from about $C_1$ to about $C_3$ alkyl.

In practicing certain aspects of the invention a β-lactam having a first and a second hydroxyl group can be formed by treatment of a fully protected dihydroxy substituted β-lactam with a weak base to selectively cleave the protecting group from the hydroxyl bonded to the N-1 position. The phosphite triester can be treated with a capping reagent prior to oxidation. The phosphite triester can be oxidized to a phosphate triester or to a phosphorothioate.

DESCRIPTION OF PREFERRED EMBODIMENTS

The monomeric compounds of the invention each include a β-lactam moiety that is substituted at the N-1, C-3, and C-4 positions with tethered or untethered functional groups as shown in formula I and II. Preferred substitutions at the C-3 position can include naturally occurring nucleobases e.g. thymine, adenine, cytosine, guanine, and uracil as well as non naturally occurring nucleobases and other functional moieties. Substitutions at the C-3 position can also include an optional $A_m$ group. The $B_m$ group serves as a functional moiety. The $A_m$ group can serve as a functional moiety or it can serve as a tether for the $B_m$ group. Hydroxyl groups are included at the N-1 and C-4 positions either with or without alkyl groups that act as tethers or space spanning groups. These hydroxyls can mimic the 3' and 5' hydroxyls of a deoxyribonucleotide in that they can be used to link the β-lactam rings in a manner analogous to nucleotides. They can be linked to solid support, other β-lactams through phosphate linking moieties, or to other groups as is practiced in the synthesis of conventional oligonucleotides.

The use of protecting groups of varying reactivities for the hydroxyls attached directly or indirectly to the C-4 and the N-1 position and for groups on the $B_m$ and or $A_m$ groups attached to the C-3 position during the synthesis, enables selective deprotection. Thus, the hydroxyl group at the N-1 position can be protected allowing it to be selectively cleaved such as by using a fluoride source such as HF/pyridine for a $R_3Si$ protecting group, or KCN in the case of an acetyl protecting group, leaving the functional groups at the C-3 and C-4 position protected. The resulting free hydroxyl group at the N-1 position may be further reacted with an activated solid support or functionalized to the phosphoramidite. As will be evident to those skilled in the art a number of oligomeric compounds can be synthesized using these synthons.

The β-lactam protected phosphoramidite e.g. a DMT-phosphoramidite, is used analogously to the DMT-phosphoramidite of a deoxyribonucleotide making the present invention amenable to all the chemistries used in the assembly of oligodeoxy-nucleotides e.g. phosphotriester, H-phosphonate, and others.

The present invention presents novel β-lactamsides, β-lactamtides, and oligo-β-lactamtides e.g. β-lactam nucleic acids. The oligo-β-lactamtides can be prepared entirely of β-lactam monomers or they can be prepared to include other monomeric units e.g. ribonucleotides and analogs thereof or peptide nucleic acids and analogs thereof wherein at least one of the monomers of the resulting oligomeric composition is a β-lactam monomer of the invention.

Synthesis of the β-lactamsides, β-lactamtides, and oligo-β-lactamtides is preferably by a stepwise procedure wherein intermediates are prepared and reacted sequentially with each other. The procedures described below represent certain preferred embodiments and correspond to the following schemes.

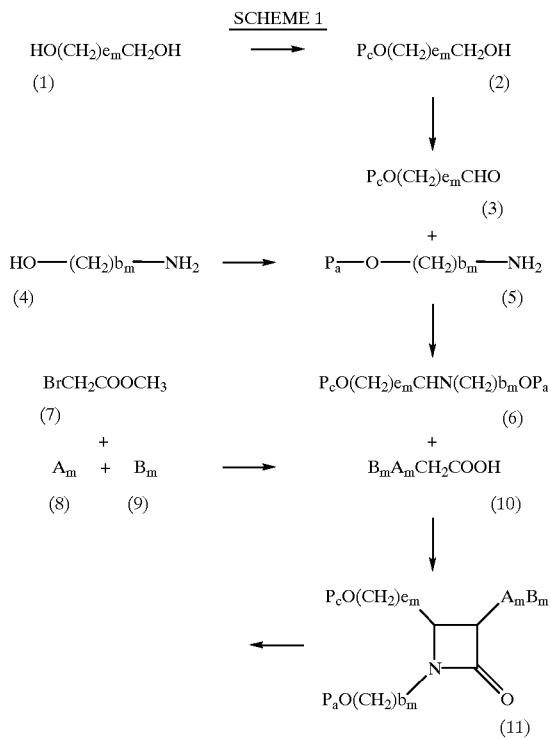

SCHEME 1

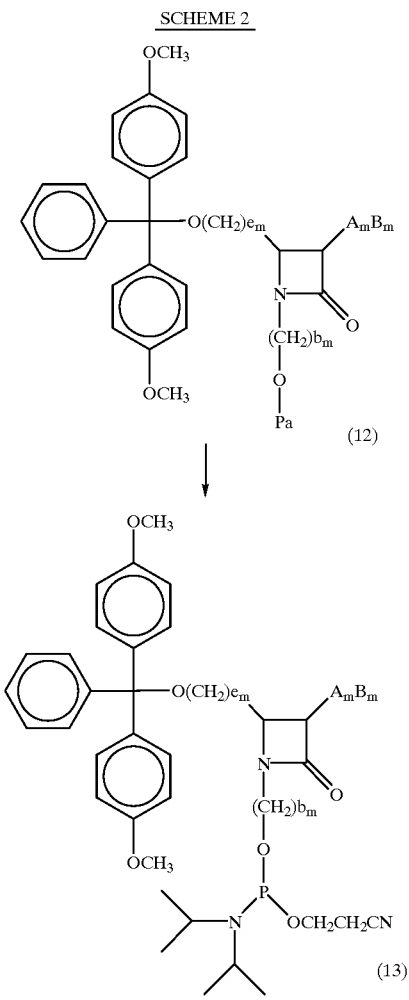

SCHEME 2

An alkyl diol, 1 is protected using an $R_3Si$- type protecting group e.g. TBDMS, to give the monoprotected diol, 2. The monoprotected diol is oxidized to the aldehyde, 3 via e.g. a Swern oxidation. In a separate synthesis an alkyl hydroxyl amine, 4 is protected with a weak base labile protecting group e.g. acetyl, to give, 5 which is further reacted with the aldehyde, 3 to give a diprotected imine, 6 or an oxime when $b_m=0$ e.g. there is no ($CH_2$) between N and $OP_a$ in the imine, 6. A bromoalkylmethyl ester is optionally reacted with an $A_m$, 8 as described above, followed by reaction with $B_m$, 9 (e.g. a nucleobase, a modified nucleobase, or other group as discussed above) that is protected if necessary, to give a B-A-alkyl carboxy compound, 10 wherein A is optional. The B-A-alkyl carboxy compound is further reacted with the diprotected imine or oxime, 6 to give a substituted β-lactam, 11 through an acid chloride imine or oxime condensation or by ketene oxime condensation. The substituted β-lactam is converted into the phosphoramidite, 13 by first selectively removing the $P_c$ protecting group e.g. TBDMS, which can be selectively removed by a fluoride source leaving other acid labile and base labile protecting groups used in the synthesis unaffected and then reacting the resultant free hydroxyl with an acid labile protecting group used in standard oligodeoxy-nucleotide synthesis e.g. dimethoxytrityl, to give the trityl protected β-lactam, 12. Removal of the $P_a$ protecting group with a nucleophilic group such as cyanide ion followed by reaction with a standard amidite reagent like (β-cyanoethoxy)-chloro-N,N-diisopropylamino)phosphine gives the phosphoramidite of the substituted-β-lactam.

It can readily be seen that by altering the starting materials a large number of diverse structures can be synthesized. The use of different $A_m$ groups will modify the distance from the β-lactam backbone to the Base moiety ($B_m$) When $A_m$ is not incorporated as a separate entity, it may still be incorporated by altering the ester, 7. A small alkyl chain can be incorporated as for instance using methyl bromoproprionate to give $A_m$ equal to $CH_2$ or using methyl bromobutyrate as the ester to give $A_m$ equal to $C_2H_4$. Altering the number of alkyl spacing groups e.g. $e_m$ and $b_m$, will effect the overall length of the final oligomer. As illustrated in the below examples, there are numerous reagents available with protecting groups e.g. benzyl amines and benzyl esters that may be used in the synthesis without a prior protecting step. Holding the $e_m$, $b_m$ and $A_m$ groups constant and altering the base moiety ($B_m$) used in the synthesis will also provide a large number of diverse compounds.

Lactam Nucleic Acids as Oligomers

The compounds of the present invention may also be described as oligomers wherein at least one of the subunits thereof is a β-lactam nucleic acid of the structure:

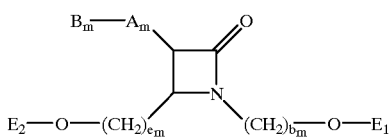

II wherein $A_m$, $B_m$, $E_1$, $E_2$, $e_m$, and $b_m$ have the same meaning as defined above. The term "subunits" as used herein, refers to β-lactam nucleic acid moieties that can form polymers and to naturally occurring nucleotides and nucleotide analogs as well as other commonly used monomers that are routinely used for preparing oligomeric stuctures using standard methods and techniques. Such repeating subunits form polymers referred to as "oligomers", and this term, as used herein, may refer to oligomers in which substantially all subunits of the oligomer are β-lactam subunits as illustrated above. Oligomers of the present invention may also comprise one or more subunits that are not β-lactam subunits e.g. naturally occurring nucleotides, nucleotide analogs, or other commonly used monomers as long as at least one subunit is a β-lactam nucleic acid. Thus, oligomers as used herein may refer to a range of oligomers from oligomers having only one β-lactam nucleic acid subunit to oligomers in which every subunit is a β-lactam nucleic acid subunit.

Those subunits which are not β-lactam nucleic acid subunits comprise naturally occurring bases, sugars, and intersugar (backbone) linkages as well as non-naturally occurring portions. Sequences of oligomers of the present invention are defined by reference to the B group (for β-lactam nucleic acid subunits) or nucleobase (for nucleotide subunits) at a given position. Thus, for a given oligomer, the nomenclature is modeled after traditional nucleotide nomenclature, identifying each β-lactam nucleic acid subunit by the identity of its B group, such as the heterocycles adenine (A), thymine (T), guanine (G) and cytosine (C) and identifying nucleotides or nucleosides by these same heterocycles residing on the sugar backbone. The sequences are conveniently provided in traditional 5' to 3' direction.

Oligomers of the present invention may range in length from about 2 to about 60 subunits. In other embodiments of the present invention, oligomers may range in length from about 2 to about 40 subunits. In still other embodiments of the present invention oligomers may range in length from about 2 to about 20 subunits. In yet further embodiments of the present invention, oligomers may range in size from about 6 to about 18 subunits in length.

β-Lactam phosphoramidites of structure I are used to form oligomeric structures of the invention wherein, the $A_m$, $B_m$, $e_m$, and $b_m$, are as described above and $E_1$ is an activated phosphite and $E_2$ is an acid labile hydroxyl protecting group e.g. dimethoxytrityl chloride. The subunits or phosphoramidites of the invention are covalently linked with phosphate linkages using standard solid and solution phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphites. The phosphoramidites utilize $P^{III}$ chemistry. The intermediate phosphite compounds are subsequently oxidized to the $P^V$ state using known methods. This permits synthesis of the preferred phosphodiester or phosphorothioate phosphate linkages depending upon oxidation conditions selected. Other phosphate linkages that can be prepared include phosphorodithioates, phosphotriesters, alkyl phosphonates, phosphoroselenates and phosphoramidates.

One preferred synthesis of β-lactam nucleic acids of the present invention starts with attaching a β-lactam to a solid support carrier using the N-1-hydroxyl group which may include an alkyl tether. Alternatively it is possible to attach the β-lactam to the synthetic resin solid support through formation of a phosphite triester or other linkage. Thus, the β-lactam is reacted in a manner analogous to nucleosides having 3'—OH and 5'—OH groups, which are used in preparing polynucleotides, as described in, e.g., U.S. Pat. Nos. 4,458,066; 4,500,707; and 5,132,418. The 3'—OH group of the nucleoside corresponds to the 1-N-hydroxyl group of the β-lactam, while the 5'—OH group corresponds to the hydroxyl group attached to the 4-position of the β-lactam. These hydroxyls are attached to the β-lactam either with or without an alkyl tethering group. In a manner analogous to the known methods for solid support synthesis of polynucleotides, the dihydroxy β-lactam is covalently coupled to the synthetic resin solid support using a conventional coupling agent.

The nature of the reactive group which bonds the dihydroxy β-lactam to the synthetic resin support is not critical, but should preferably be readily hydrolyzable in order to permit separation of the final β-lactam nucleic acid product from the synthetic resin support at the conclusion of the preparative procedures.

It is sometimes desirable to have the coupling agents or groups present on the dihydroxy β-lactam for reaction with the reactive groups, e.g., hydroxyl or amino, on the synthetic resin support as illustrated above. Alternatively the coupling group may be located on the synthetic resin support.

A number of functional groups can be introduced into compounds of the invention in a protected (blocked) form and subsequently de-protected to form a final, desired compound. In general, protecting groups render chemical functionality inert to specific reaction conditions and can be appended to and removed from such functionality in a molecule without substantially damaging the remainder of the molecule. The βlactamsides, β-lactamtides, and oligo-β-lactamtides of the present invention are prepared utilizing protecting groups of diverse reactivity to allow stepwise removal when the desired functional group is needed. Some of the diverse types of protecting groups that are utilized in the present invention are acid and base labile protecting groups and protecting groups that are removed by a fluoride source. See, e.g., Green and Wuts, *Protective Groups in Organic Synthesis*, 2d edition, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, and trimethoxytrityl groups.

In one embodiment of the invention an oligo-β-lactamtide is prepared using a solid support carrier. The desired β-lactam is protected at the C-4-hydroxyl position with an acid labile protecting group and at the N-1-hydroxyl position with a weak base labile protecting group or other protecting group that can be removed without effecting the acid labile and strong base labile protecting groups. Other functional groups that do not participate in the oligomerization are protected with strong base labile protecting groups. Strong base labile protecting groups are removed by treatment with a strong base e.g. 30% ammonium hydroxide as is used for standard DNA synthesis. The 1-N-hydroxyl group is selectively deprotected using a weak base e.g. KCN as illustrated in the examples below. To attach the β-lactam to the solid support carrier it is necessary to couple N-1-hydroxyl of the β-lactam with a bifunctional group. When the bifunctional group is attached to the β-lactam it is further activated with an activating group and reacted with a solid support using standard methods e.g. *Oligonucleotide Synthesis, A Practical Approach*, Gait. M, J., Ed., IL: New York., 1984, Chapter 1; Masad J. Damha, *nucleic acids research*, 1990, 18, 3813–3821. One reagent commonly used in DNA synthesis is succinic anhydride which is reacted with the monomeric compound of interest and then activated with a leaving group e.g. pentafluorophenol or para nitrophenol and further reacted with a functional group on the solid support e.g. $NH_2$ on LCAA CPG. A capping step is performed using a suitable capping agent e.g. acetic anhydride/lutidine/THF, and N-methyl imidazole/THF to cap any remaining reactive sites. The acid labile protecting group on the 4-hydroxyl position is removed with a dilute acid solution e.g. dichloroacetic acid or trichloroacetic acid to give the free hydroxyl at the 4 position. The solid support carrier is washed with a suitable solvent e.g. acetonitrile. The next step in the process is to couple the free hydroxyl group with the phosphoramidite group of a synthon comprising a phosphoramidite group covalently bound to a β-lactam having the desired protected nucleobase substituent. The resulting carrier bound dimer is oxidized from the phosphite to the phosphate to give either a phosphate triester or a phosphorothioate depending on the oxidizing reagent. The various types of phosphoramidite groups suitable for use in preparing the β-lactam nucleic acids of the present invention have been described above.

The desired phosphoramidite/β-lactam synthon may be prepared by forming the corresponding chloro-(2'-amino) alkoxyphosphine and thereafter condensing this product directly with the selected βlactam. The reaction is carried out in an organic solvent solution of the selected β-lactam, preferably in the presence of a tertiary amine to take up the hydrogen chloride formed in the condensation reaction. The reaction proceeds smoothly at room temperature in a dry atmosphere and under an inert gas such as nitrogen or helium. Organic solvents useful for this reaction include any solvent which will dissolve the reactants, such as acetonitrile, diethylether, chloroform, methylene chloride, ethylene chloride, ethyl acetate, and the like. The solution containing the product is separated from the precipitated hydrochloride salt of the added tertiary amine, and can be used as such in forming β-lactam nucleic acids, or alternatively can be separated from the solvent and purified by crystallization before further use.

Alternatively, formation of a phosphoramidite/β-lactam synthon may be achieved simply by coupling the free primary 4-hydroxyl group of the β-lactam with a phosphoramidite group of another suitable synthon by condensing the selected β-lactam with the phosphoramidite synthon in a suitable solvent and in the presence of an organic base such as 1-H-tetrazole. Such procedures are described, e.g., in Thuong and Chassignol, *Tetrahedron Lett.*, 1987, 28, 4157; and Horn and Urdea, *Tetrahedron Lett.*, 1986, 27, 4705. It is helpful in this reaction to use proton donors which activate the phosphoramidites. For example, acidic compounds may be used, and are preferably mildly acidic and include amine hydrohalide salts and nitrogen heterocyclic compounds such as tetrazoles, imidazoles, nitroimidazoles, benzimidazoles, and similar nitrogen heterocyclic proton donors. The amine hydrohalide salts to be used for the protonation activation are preferably tertiary amine salts, and preferably, the hydrochloride salts, although hydrobromide, hydroiodide or hydrofluoride salts can also be used. The tertiary amines include, e.g., dimethylaniline, diisopropylaniline, methylethylaniline, methyldiphenylamine, pyridine and similar teritary amines.

Once the selected β-lactam has been successfully coupled to the phosphoramidite of choice, the next step of the process is oxidizing the resulting phosphite triester to the P(V) phosphate state with oxygen or sulfur.

Such oxidation can be carried out for both phosphate (Y=O) and phosphorothioate (Y=S) structures. The oxidation can be carried out using iodine as the oxidizing agent and under standard procedures. Oxidation can also be accomplished by reaction with peroxides such as t-butyl peroxide and benzoyl peroxide, as well as hydroperoxides. The use of hydrogen peroxide can lead to the formation of side products, and is, therefore, not preferred. Oxidation should be carried out before further condensation of β-lactam synthons is attempted, in order to obtain the best yields. Attempts to defer oxidation until after all condensation reactions are completed, have resulted in reduced yields of product in analogous oligonucleotide preparations, due to the formation of side products.

Useful sulfurizing agents include the Beaucage reagent described in e.g., Iyer et al., *J Am Chem Soc*, 112, 1253–1254 (1990); and Iyer et al., *J Org Chem*, 55, 4693–4699 (1990); tetraethyl-thiuram disulfide as described in Vu et al., *Tetrahedron Lett*, 32, 3005–3007 (1991); dibenzoyl tetrasulfide as described in Rao et al., *Tetrahedron Lett*, 33, 4839–4842 (1992); di(phenylacetyl)disulfide, as described in Kamer, et al., Tetrahedron Lett, 30, 6757–6760 (1989); bis(O,O-diisopropoxy phosphinothioyl)disulfide, Wojciech J. Stec., *Tetrahedron Letters*, 1993, 34, 5317–5320; sulfur; and sulfur in combination with ligands like triaryl, trialkyl or triaralkyl or trialkaryl phosphines. Useful oxidizing agents, in addition to those set out above, include iodine/tetrahydro-furan/water/pyridine; hydrogen peroxide/water; tert-butyl hydroperoxide; or a peracid like m-chloroperbenzoic acid. In the case of sulfurization, the reaction is performed under anhydrous conditions with the exclusion of air, in particular oxygen; whereas, in the case of oxidation the reaction can be performed under aqueous conditions.

Once the oxidation step has been completed the next step is to block any unreacted sites such as hydroxyl groups that didn't react previously. This step is referred to as the capping step and it is routinely performed after oxidation but can be performed out of sequence depending on the synthesis being performed. The solid support is treated with a capping reagent and washed with a suitable solvent.

More traditional blocking or capping groups can be employed, such as acid anhydrides, e.g., acetic anhydride, and arylisocyanates, and phenyl isocyanate. When acetylation with acid anhydrides, e.g., acetic anhydride, is conducted in the presence of tertiary amines, especially di-loweralkylamino-pyridines such as dimethylaminopyridine, acylation occurs rapidly and this procedure is preferred for blocking, especially the N-hydroxy group of the β-lactam. The dialkylphosphite capping group can also be used. The resulting triester is relatively nonhydrophobic and a preferred purification involves reverse phase high performance liquid chromatography which assures separation of the nonhydrophobic byproduct from the product containing the hydrophobic N-O-dimethoxytrityl group.

Methods of Using β-Lactam Nucleic Acids

The β-lactam nucleic acids of the present invention may be used for research and in diagnostics for detection and isolation of specific nucleic acids. For example, they may be utilized in studies of enzyme biochemistry and protein-nucleic acid interactions. These and other applications are listed in "Oligonucleotides and Analogues: A Practical Approach", F. Eckstein Ed., IRL Press, at pages 88–91, and in the references contained therein, which are hereby incorporated by reference.

As a further aspect of the invention, βlactam nucleic acids can be used to target RNA and ssDNA. When so used β-lactam nucleic acids are useful as hybridization probes for the identification and purification of nucleic acids and as therapeutic agents. Furthermore, the β-lactam nucleic acids can be modified in such a way that they can form triple helices with dsDNA. Further reagents that bind sequence-specifically to dsDNA have applications as gene targeting therapeutic agents. These are foreseen as extremely useful for treating infections and other like diseases, and may also prove effective for treatment of some genetic diseases. The β-lactam nucleic acids of the invention can be used in diagnostics, therapeutics and as research reagents and kits. They can be used in pharmaceutical compositions by including a suitable pharmaceutically acceptable diluent or carrier. They can be used for treating organisms having a disease characterized by the undesired production of a protein. The organism should be contacted with a β-lactam nucleic acid having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic β-lactam nucleic acids. As used herein, therapeutics is meant to include the eradication of a disease state, by killing an organism or by control of erratic or harmful cellular growth or expression.

The triple helix principle is believed to be the only known principle in the art for sequence-specific recognition of dsDNA. However, triple helix formation is largely limited to recognition of homopurine-homopyrimidine sequences. Strand displacement is superior to triple helix recognition in that it allows for recognition of any sequence by use of the four natural bases. Also, in strand displacement recognition readily occurs at physiological conditions, that is, neutral pH, ambient (20–40° C.) temperature and medium (100–150 mM) ionic strength.

Gene targeted drugs are designed with a nucleobase sequence (containing 10–20 units) complementary to the regulatory region (the promoter) of the target gene. Therefore, upon administration of the drug, it binds to the promoter and blocks access thereto by RNA polymerase. Consequently, no mRNA, and thus no gene product (protein), is produced. If the target is within a vital gene for a virus, no viable virus particles will be produced. Alternatively, the target could be downstream from the promoter, causing the RNA polymerase to terminate at this position, thus forming a truncated mRNA/protein which is nonfunctional.

Where the β-lactam nucleic acids of the present invention are used as therapeutic agents to treat a disease as described further above, they are administered to a host in need of such treatment formulated in a pharmaceutical composition. Such a pharmaceutical composition can include carriers, thickeners, diluents, buffers, preservatives, surface active agents and the like in addition to the oligomer. Pharmaceutical compositions also can include one or more active ingredients such as antimicrobial agents, anti-inflammatory agents, anesthetiimine cs, and the like in addition to the β-lactam nucleic acid.

The pharmaceutical composition can be administered in a number of ways depending on whether local or systemic treatment is desired, and on the area to be treated. Administration can be topically (including transdermally, opthalmically, vaginally, rectally, intranasally), orally, by inhalation, or parenterally, for example by intravenous drip, subcutaneous, intraperitoneal or intramuscular injection.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration can include sterile aqueous solutions which also can contain buffers, diluents and other suitable additives.

Dosing is dependent on severity and responsiveness of the condition to be treated, but will normally be one or more doses per day, with the course of treatment lasting from several days to several months or until a cure is effected or a diminution of disease state is achieved. Persons of ordinary skill can easily determine optimum dosages, dosing methodologies and repetition rates.

Additional objects, advantages, and novel features of this invention will become apparent to those skilled in the art upon examination of the following examples thereof, which are not intended to be limiting.

EXAMPLE 1

N-1-Carboxymethylthymine

To a suspension of thymine (0.317 mole) and potassium carbonate (0.634 mole) in dimethylformamide (900 ml) is added methyl bromoacetate (0.634 mole) and the mixture is stirred vigorously overnight under nitrogen. The mixture is filtered, washed with ether and evaporated to dryness, in vacuo to afford a colorless solid. The solid residue is treated with water (300 ml) and 4 N hydrochloric acid (12 ml), stirred for 20 minutes at 0° C., filtered and washed with water (2×100 ml). The precipitate is treated with water and 2 N sodium hydroxide (60 ml), and is boiled for 10 minutes. The mixture is cooled at 0° C., filtered, and then pricipitated by the addition of 4 N hydrochloric acid (70 ml) to give the title compound.

EXAMPLE 2

N-4-Benzoyl-N-1-carboxymethylcytosine

To a suspension of N-4-benzoylcytosine (0.317 mole) and potassium carbonate (0.317 mole) in dimethylformamide (900 ml), is added benzyl bromoacetate (0.317 mole) and the mixture is stirred vigorously overnight under nitrogen. The mixture is filtered, washed with ether and evaporated to dryness, in vacua. The solid residue is dissolved in methanol (50 ml) and hydrogenated using Raney nickel (5 g) and hydrogen at a pressure of 40 psi for 6 hours. The reaction mixture is filtered, the catalyst washed with methanol (20 ml) and the combined fractions are concentrated to give the title compound.

EXAMPLE 3

N-9-Carboxymethyladenine Benzyl Ester

Adenine (74 mmole) and potassium carbonate (74 mmole) are suspended in DMF (100 ml) and benzyl bromoacetate (74 mmole) in DMF (20 ml) is added. The suspension is stirred for 3 hours under nitrogen at room temperature, and then filtered. The solid residue is washed three times with DMF (25 ml), and the combined filtrate is evaporated to dryness, in vacua to give the title compound.

EXAMPLE 4

N-6-Benzoyl-N-9-carboxymethyladenine Benzyl Ester

To a stirred solution of N-9-carboxymethyladenine benzyl ester (15 mmole) and pyridine (25 ml) in DMF (50 ml), in an ice bath, is added a solution of benzoic anhydride (60 mmole) in DMF (30 ml). The ice-bath is removed and the mixture is stirred overnight. The reaction mixture is concentrated to give the title compound as a solid.

EXAMPLE 5

N-6-Benzoyl-N-9-carboxymethyladenine

N-6-benzoyl-N-9-carboxymethyladenine benzyl ester (10 mmole) is stirred in methanol (50 ml) and hydrogenated using Raney nickel (5 g) g31 and hydrogen at a pressure of 40 psi for 6 hours. The reaction mixture is filtered and the catalyst is washed with methanol (20 ml). The combined fractions are concentrated to give the title compound as a solid.

EXAMPLE 6

N-9-Carboxmethylguanine Benzyl Ester

Guanine (74 mmole) and potassium carbonate (74 mmole) are suspended in DMF (100 ml) and benzyl bromoacetate (74 mmole) in DMF (20 ml) is added. The suspension is stirred for 3 hours under nitrogen at room temperature, and then filtered. The solid residue is washed three times with DMF (25 ml), and the combined filtrate is evaporated to dryness, in vacuo, to give the title compound.

EXAMPLE 7

N-Benzoyl-N-9-carboxymethylguanine Benzyl Ester

To a stirred solution of N-9-carboxymethyladenine benzyl ester (15 mmole) and pyridine (25 ml) in DMF (50 ml) is added a solution of benzoic anhydride (60 mmole) in DMF (30 ml) with ice-cooling. The ice-bath is removed and the reaction mixture is stirred overnight. The reaction mixture is concentrated to give the title compound as a solid.

EXAMPLE 8

N-Benzoyl-N-9-carboxymethylguanine

N-Benzoyl-N-9-carboxymethyladenine benzyl ester (10 mmole) is taken up in methanol (50 ml) and hydrogenated using Raney nickel (5 g) and hydrogen at a pressure of 40 psi for 6 hours. The reaction mixture is filtered, the catalyst washed with methanol (20 ml) and the combined methanol fractions are concentrated to give the title compound as a solid.

EXAMPLE 9

Preparation of Imine

O-Benzylhydroxylamine (40 mmole) is dissolved in dichloromethane (150 ml), and a solution of benzyloxyacetaldehyde (40 mmole) in dichloromethane (50 ml) is added slowly under nitrogen at 0° C. The reaction mixture is stirred for 30 minutes and then 4 A molecular sieves (15 g) are added to it. After stirring for 4 hours, the reaction mixture is filtered and concentrated to give the title compound.

EXAMPLE 10

1-N-Benzyloxy-3-(thymidin-1-yl)-4-benzyloxymethyl-2-azetidinone

To a stirred suspension of N-1-carboxymethylthymine (20 mmole) in DMF (50 ml) is added 2-chloro-1-methylpyridiniumiodide (20 mmole). The reaction mixture is heated gently till the solution becomes homogenous. The reaction mixture is slowly cooled to room temperature and then a solution of imine (prepared in Example 9), (20 mmole) in DMF (20 ml) is added slowly over a period of 20 minutes. The reaction mixture is stirred overnight and concentrated under vacuo. The crude product is purified by flash chromatography over silica gel to give title compound as a crystalline solid.

EXAMPLE 11

1-N-Benzyloxy-3-(N-benzoylcytosin-1-yl)-4-benzyloxymethyl-2-azetidinone

To a stirred suspension of N-4-benzoyl-N-1-carboxymethylcytosine (20 mmole) in DMF (50 ml) is added 2-chloro-1-methylpyridiniumiodide (20 mmole). The reaction mixture is heated gently till the solution becomes homogenous. The reaction mixture is slowly cooled to room temperature and then a solution of imine (prepared in Example 9) (20 mmole) in DMF (20 ml) is added slowly over a period of 20 minutes. The reaction mixture is stirred overnight and concentrated under vacuo. The crude product is purified by flash chromatography over silica gel to give the the title compound as a crystalline solid.

EXAMPLE 12

1-N-Benzyloxy-3-(N-benzoyladenin-9-yl)-4-benzyloxymethyl-2-azetidinone

To a stirred suspension of N-6-benzoyl-N-1-carboxymethyl-adenine (20 mmole) in DMF (50 ml) is added 2-chloro-1-methylpyridiniumiodide (20 mmole). The reaction mixture is heated gently till the solution becomes homogenous. The reaction mixture is slowly cooled to room temperature and then a solution of imine (prepared in Example 9) (20 mmole) in DMF (20 ml) is added slowly over a period of 20 minutes. The reaction mixture is stirred overnight and concentrated under vacuoc. The crude product is purified by flash chromatography over silica gel to give the title compound as a crystalline solid.

EXAMPLE 13

1-N-Benzyloxy-3-(N-benzoylguanin-9-yl)-4-benzyloxymethyl-2-azetidinone

To a stirred suspension of N-2-benzoyl-N-1-carboxymethylguanine (20 mmole) in DMF (50 ml) is added 2-chloro-1-methyl-pyridiniumiodide (20 mmole). The reaction mixture is heated gently till the solution becomes homogenous. The reaction mixture is slowly cooled to room temperature and then a solution of imine (prepared in Example 9) (20 mmole) in DMF (20 ml) is added slowly over a period of 20 minutes. The reaction mixture is stirred overnight and concentrated under vacuo. The crude product is purified by flash chromatography over silica gel to give the title compound as a crystalline solid.

EXAMPLE 14

1-N-Hydroxy-3-(thymidin-1-yl)-4-hydroxymethyl-2-azetidinone

1-N-Benzyloxy-3-(thymidin-1-yl)4-benzyloxymethyl-2-azetidinone (10 mmole) is taken up in methanol (50 ml) and hydrogenated using Raney nickel (5 g) and hydrogen at a pressure of 40 psi for 6 hours. The reaction mixture is filtered, the catalyst washed with methanol (20 ml) and the combined fractions are concentrated to to give the title compound as a solid.

EXAMPLE 15

1-N-Hydroxy-3-(N-benzoylcytosin-1-yl)-4-hydroxymethyl-2-azetidinone

1-N-Benzyloxy-3-(N-benzoylcytosin-1-yl)-4-benzyloxymethyl-2-azetidinone (10 mmole) is taken up in methanol (50 ml) and hydrogenated using Raney nickel (5 g) and hydrogen at a pressure of 40 psi for 6 hours. The reaction mixture is filtered, the catalyst washed with methanol (20 ml) and the combined fractions are concentrated to afford the product as a solid.

EXAMPLE 16

1-N-Hydroxy-3-(N-benzoyladenin-9-yl)-4-hydroxymethyl-2-azetidinone

1-N-Benzyloxy-3-(N-benzoyladenin-9-yl)-4-benzyloxymethyl-2-azetidinone (10 mmole) is taken up in methanol (50 ml) and hydrogenated using Raney nickel (5 g) and hydrogen at a pressure of 40 psi for 6 hours. The reaction mixture is filtered, the catalyst washed with methanol (20 ml) and the combined methanol fractions are concentrated to give the title compound as a solid.

EXAMPLE 17

1-N-Hydroxy-3-(N-benzoylguanin-9-yl)-4-hydroxymethyl-2-azetidinone

1-N-Benzyloxy-3-(N-benzoylguanin-9-yl)-4-benzyloxymethyl-2-azetidinone (10 mmole) and methanol (50 ml) is hydrogenated using Raney nickel (5 g) and hydrogen at a pressure of 40 psi for 6 hours. The reaction mixture is filtered, the catalyst washed with methanol (20 ml) and the combined methanol fractions are concentrated to give the title compound as a solid.

EXAMPLE 18

1-N-Hydroxy-3-(thymidin-1-yl)-4-(4,4-dimethoxytrityloxymethyl)-2-azetidinone

1-N-Hydroxy-3-(thymidin-1-yl)-4-hydroxymethyl-2-azetidinone (10 mmole) is dissolved in pyridine (20 ml) and 4,4'-dimethoxytrityl chloride (12 mmole) is added and stirred under argon for 8 hours. The reaction mixture is concentrated under reduced pressure. The crude product is purified by flash chromatorgraphy using silica gel and ethyl acetate/dichloromethane/1% triethyl amine as eluants to give the title compound.

EXAMPLE 19

1-N-Hydroxy-3-(N-benzoylcytosin-1-yl)-4-(4,4'-dimethoxytrityloxymethyl)-2-azetidinone 1-N-Hydroxy-3-(N-benzoylcytosin-1-yl)-4-hydroxymethyl-2-azetidinone (10 mmole) is dissolved in pyridine (20 ml) and 4,4'-dimethoxytrityl chloride (12 mmole) is added and stirred under argon for 8 hours. The reaction mixture is concentrated under reduced pressure. The crude product is purified by flash chromatorgraphy using silica gel and ethyl acetate/dichloromethane/1% tri-ethylamine as eluants to give the title compound.

EXAMPLE 20

1-N-Hydroxy-3-(N-benzoyladenin-9-yl)-4-(4,4'-dimethoxytrityloxymethyl)-2-azetidinone 1-N-Hydroxy-3-(N-benzoyladenin-9-yl)-4-hydroxymethyl-2-azetidinone (10 mmole) is dissolved in pyridine (20 ml) and 4,4'-dimethoxytrityl chloride (12 mmole) is added and stirred under argon for 8 hours. The reaction mixture is concentrated under reduced pressure. The crude product is purified by flash chromatorgraphy using silica gel and ethyl acetate/di-chloromethane/1% tri-ethylamine as eluants to give the title compound.

EXAMPLE 21

1-N-Hydroxy-3-(N-benzoylguanin-9-yl)-4-(4,4'-dimethoxytrityloxymethyl-2-azetidinone 1-N-Hydroxy-3-(N-benzoylguanin-9-yl)-4-hydroxymethyl-2-azetidinone (10 mmole) is dissolved in pyridine (20 ml) and 4,4'-dimethoxytrityl chloride (12 mmole) is added and stirred under argon for 8 hours. The reaction mixture is concentrated under reduced pressure. The crude product is purified by flash chromatorgraphy using silica gel and ethyl acetate/dichloromethane/1% triethylamine as eluants to give the title compound.

EXAMPLE 22

3-(thymidin-1-yl)-4-(4,4'-dimethoxytrityloxymethyl)-2-azetidinone-1-N-O-(2-cyanoethyl N,N-diisopropylphosphoramidite)

To a solution of 1-N-hydroxy-3-(thymidin-1-yl)-4-(4,4'-dimethoxytrityloxymethyl)-2-azetidinone (12 mmole) in acetonitrile (30 ml) is added diisopropylammonium tetrazolide (12 mmole) followed by 2-cyanoethyl bis(N,N-diisopropyl)phosphoramidite (18 mmole) in acetonitrile (20 ml). The reaction mixture is stirred under argon at room temperature for 2 hours. The reaction mixture is diluted with ethylacetate (75 ml) washed with dilute sodium hydrogen carbonate (20 ml) and brine, then dried and concentrated. The crude product is purified by flash chromatography using silica gel and ethyl acetate/dichloromethane as eluants to give the title compound as a solid.

EXAMPLE 23

3-(N-benzoylcytosin-1-yl)-4-(4,4'-dimethoxytrityloxymethyl)-2-azetidinone-1-N-O-(2-cyanoethyl N,N-diisopropylphosphoramidite)

To a solution of 1-N-hydroxy-3-(N-benzoylcytosin-1-yl)-4-(4,4'-dimethoxytrityloxymethyl)-2-azetidinone (12 mmole) in acetonitrile (30 ml) is added diisopropylammonium tetrazolide (12 mmole) followed by 2-cyanoethyl bis(N,N-diisopropyl)phosphoramidite (18 mmole) in acetonitrile (20 ml). The reaction mixture is stirred under argon at room temperature for 2 hours. The reaction mixture is diluted with ethylacetate (75 ml), washed with dilute sodium hydrogen carbonate (20 ml) and brine then dried and concentrated. The crude product is purified by flash chromatography using silica gel and ethyl acetate/dichloromethane as eluants to give the title compound as a solid.

EXAMPLE 24

3-(N-benzoyladenin-9-yl)-4-(4,4'-dimethoxytrityloxymethy)-2-azetidinone-1-N-O-(2-cyanoethyl N,N-diisopropylphosphoramidite)

To a solution of 1-N-hydroxy-3-(N-benzoyladenin-9-yl)-4-(4,4'-dimethoxytrityloxymethyl)-2-azetidinone (12 mmole) in acetonitrile (30 ml) is added diisopropylammonium tetrazolide (12 mmole) followed by 2-cyanoethyl bis(N,N-diisopropyl) phosphoramidite (18 mmole) in acetonitrile (20 ml). The reaction mixture is stirred under argon at room temperature for 2 hours. The reaction mixture is diluted with ethylacetate (75 ml), washed with dilute sodium hydrogen carbonate (20 ml) and brine then dried and concentrated. The crude product is purified by flash chromatography using silica gel and ethyl acetate/dichloromethane as eluants to to give the title compound as a solid.

EXAMPLE 25

3-(N-benzoylguanin-9-yl)-4-(4,4'-dimethoxytrityloxymethy)-2-azetidinone-1-N-O-(2-cyanoethyl N,N-diisopropylphosphoramidite)

To a solution of 1-N-hydroxy-3-(N-benzoylguanin-9-yl)-4-(4,4'-dimethoxytrityloxymethyl)-2-azetidinone (12 mmole) in acetonitrile (30 ml) is added diisopropylammonium tetrazolide (12 mmole) followed by 2-cyanoethyl bis((N,N-diisopropyl)-phosphoramidite (18 mmole) in acetonitrile (20 ml). The reaction mixture is stirred under argon at room temperature for 2 hours. The reaction mixture is diluted with ethylacetate (75 ml), washed with dilute sodium hydrogen carbonate (20 ml) and brine then dried and concentrated. The crude product is purified by flash chromatography using silica gel and ethyl acetate/dichloromethane as eluants to give the title compound as a solid.

EXAMPLE 26

Preparation of 2-azetidinone-1-N-O-succinate and 2-azetidinonederivatized Controlled Pore Glass To a stirred solution of 1-N-hydroxy-3-(thymidin-1-yl)-4-(4,4'-dimethoxytrityloxymethyl)-2-azetidinone (3.0 mmole) in anhydrous pyridine (10 ml) containing 4-dimethylaminopyridine (0.180 g, 1.5 mmole) is added succinic anhydride (0.24 g, 2.4 mmole) in portions over 30 minutes. After stirring overnight, the reaction mixture is concentrated under reduced pressure to afford a gum. Toluene (30 ml) is added and co-evaporated. This co-evaporation is repeated twice (2×30 ml) with toluene. The residue is dissolved in dichloromethane (25 ml) and washed with ice-cold, 10% aqueous, citric acid and water and then dried. The organic extract is concentrated to give a foam which is precipitated at room temperature into rapidly stirring hexane (300 ml). The mixture is centrifuged, the clear supernatant decanted and the powder dried under vacuum.

The succinylated 2-azetidinone is dissolved in dioxane (10 ml). Anhydrous pyridine (1 ml) and p-nitrophenol (0.2 g) are added followed by dicyclohexylcarbodiimide (0.6 g, 2.5 mmole). Stirring is continued for 3 hours. The dicyclohexylurea formed is filtered and the filtrate is added to controlled pore glass (5 g) suspended in dimethylformamide (5 ml). Triethylamine (2 ml) is added and briefly shaken. After leaving it overnight, the CPG is filtered, washed with methanol, ether and air dried.

EXAMPLE 27

Synthesis of 5-bL(GACT)-1 Phosphorothioate Tetramer

1-N-Hydroxy-3-(thymidin-1-yl)-4-(4,4'-dimethoxytrityloxymethyl)-2-azetidinone (2 mmole) bonded to CPG (controlled pore glass) through an ester linkage is taken in a glass reactor, and a dichloromethane solution of 2% dichloroacetic acid (volume/volume) is added to deprotect the 5-hydroxyl group. The product is washed with acetonitrile. Then, a 0.2 M solution of 3-(N-benzoylcytosin-1-yl)-4-(4,4'-dimethoxytrityloxymethyl)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 5-hydroxyl groups. The product is washed with acetonitrile.

A dichloromethane solution of 2% dichloroacetic acid (volume/volume) is added to deprotect the 5-hydroxyl group. The product is washed with acetonitrile. Then, a 0.2 M solution of 3-(N-benzoyladeninyl)-4-(4,4'-dimethoxytrityloxymethyl)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl group. The product is washed with acetonitrile.

A dichloromethane solution of 2% dichloroacetic acid (volume/volume) is added to deprotect the 5-hydroxyl group. The product is washed with acetonitrile. Then, a 0.2 M solution of 3-(N-benzoylguanin-9-yl)-4-(4,4'-dimethoxytrityloxymethyl)-2-azetidinone-1-N-O-(2-cyanoethyl N,N-diisopropylphosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8). Then N-methyl imidazole/THF is added to cap the unreacted 5-hydroxyl group. The product is washed with acetonitrile.

The carrier containing the compound is treated with 30% ammonium hydroxide solution for 2×90 minutes at room temperature. The aqueous solution is filtered, concentrated under reduced pressure to give a phosphorothioate tetramer of 5-bL(GACT)-1.

EXAMPLE 28

Synthesis of 5-bL(GACT)-1 Phosphodiester Tetramer.

1-N-Hydroxy-3-(thymidin-1-yl)-4-(4,4'-dimethoxytrityloxymethyl)-2-azetidinone (2 mmole) bonded to CPG (controlled pore glass) through an ester linkage is placed in a glass reactor, and a solution of 2% dichloroacetic acid in dichloromethane (volume/volume) is added to deprotect the 5-hydroxy group. The product is washed with acetonitrile. A 0.2 M solution of 3-(N-benzoylcytosin-1-yl)-4-(4,4'-dimethoxytrityloxymethyl)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile and a 0.05 M solution of tert -butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 5-hydroxyl groups. The product is washed with acetonitrile.

A solution of 2% dichloroacetic acid in dichloromethane (volume/volume) is added to deprotect the 5-hydroxyl groups. The product is washed with acetonitrile. A 0.2 M solution of 3-(N-benzoyladenin-9-yl)-4-(4,4'-dimethoxytrityloxymethyl)-2-azetidinone-1-N-O-(2-cyanoethyl N, N-diisopropylphosphoroamidite) in acetonitrile and a 0.4 M solution of 1H-tetrazole in acetonitrile is added and reacted at room temperature for 5 minutes. The product is washed with acetonitrile, and then a 0.05 M solution of tert-butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 5-hydroxyl groups. The product is washed with acetonitrile.

A solution of 2% dichloroacetic acid in dichloromethane (volume/volume) is added to deprotect the 5-hydroxyl groups. The product is washed with acetonitrile. A 0.2 M solution of 3-(N-benzoylguaninyl-9-)-4-(4,4'-dimethoxytrityloxymethyl)-2-azetidinone-1-N-O-(2-cyanoethyl N,N-diisopropylphosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of tert-butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 5-hydroxyl groups. The product is washed with acetonitrile.

The carrier containing the compound is treated with 30% ammonium hydroxide solution for 2×90 minutes at room temperature. The aqueous solution is filtered and concentrated under reduced pressure to give a phosphorothioate tetramer of 5-bL(GACT)-1.

EXAMPLE 29

Preparation of Fully Protected TT Dimer

To a solution of 1-N-acetoxy-3-(thymidin-1-)yl-4-(4,4-dimethoxytrityloxymethyl)-2-azetidinone (5.0 mmole) and 1-H tetrazole (4.0 mmole) in acetonitrile (60 ml) is added 3-(thymidin-1-yl)-4-(4,4'-dimethoxytrityloxymethyl)-2-azetidinone-1-N-O-(2-cyanoethyl N,N-diisopropylphosphoramidite) (6.0 mmole) in 40 ml acetonitrile. The reaction mixture is stirred at room temperature under argon for 0.5 hour. A solution of 3H-1, 2-benzodithiol-3-one 1,1-dioxide (5.0 g, 25 mmole) in acetonitrile is added rapidly with vigorous stirring. The reaction mixture is stirred at room temperature for 20 minutes. The reaction mixture is then filtered and concentrated. The crude product is purified by flash chromatography on silica gel using ethyl acetate/hexane with 1% triethylamine to give the dimer.

EXAMPLE 30

Preparation of the 5-HO-TT Dimer

The fully protected phosphorothioate TT dimer (1 mmol) is dissolved in dichloromethane (50 ml) and 3% dichloroacetic acid in dichloromethane (v/v) (20 ml) is added and the mixture is stirred for 15 minutes. The reaction mixture is concentrated and purified by flash chromatography on silica gel using ethyl acetate/hexane with 1% triethylamine.

EXAMPLE 31

Preparation of Fully Protected CTT Phosphorothioate trimer

To a solution of 5-HO-TT phosphorothioate dimer (5.0 mmole) and 1-H tetrazole (5.0 mmole) in acetonitrile (60 ml) is added 3-(N-benzoylcytosin-1-yl)-4-(4, 4'-dimethoxytrityloxymethyl)-2-azetidinone-1-N-O-(2-cyanoethyl N,N-diisopropylphosphoramidite) (6.0 mmol) in acetonitrile (40 ml). The reaction mixture is stirred at room temperature under argon for 0.5 hour. A solution of 3H-1, 2-benzodithiol-3one 1,1-dioxide (25 mmol) in aceto nitrile is added rapidly with vigorous stirring. The reaction mixture is stirred at room temperature for 20 minutes. The reaction mixture is then filtered and concentrated. The crude product is purified by flash chromatography on silica gel using ethyl acetate/hexane with 1% triethylamine.

EXAMPLE 32

Synthesis of 5'-d(GAC)-bL(GACT)-d(CTT)-3'-phosphorothioate DNA/LNA Mixed Sequence
<SEQ. ID. NO. 1>

5'-O-Dimethoxytritylthymidine bonded to CPG (controlled pore glass) through an ester linkage is placed in a glass reactor, and a solution of 2% dichloroacetic acid in dichloromethane (volume/volume) is added to deprotect the 5-hydroxyl groups. The product is washed with dichloromethane and then with acetonitrile. A 0.2 M solution of 5'-O-(4, 4'-dimethoxytrityl)thymidine-3'-0-(2-cyanoethyl N,N-diisopropyl-30 phosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups.

A solution of 2% dichloroacetic acid in dichloromethane (volume/volume) is added to deprotect the 5-hydroxyl groups. The product is washed with acetonitrile. A 0.2 M solution of 3-(N-benzoylcytosin-1-yl)-4-(4, 4'-dimethoxytrityloxymethy)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups. The product is washed with acetonitrile.

A dichloromethane solution of 2% dichloroacetic acid (volume/volume) is added to deprotect the 5-hydroxyl groups. The product is washed with acetonitrile. A 0.2 M solution of 3-(thymidin-1-yl)-4-(4,4'-dimethoxytrityloxymethyl)-2-azetidin-one-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups. The product is washed with acetonitrile.

A solution of 2% dichloroacetic acid in dichloromethane (volume/volume) is added to deprotect the 5-hydroxy groups. The product is washed with acetonitrile. A 0.2 M solution of 3-(N-benzoylcytosin-1-yl)-4-(4,4'-dimethoxytrityloxymethyl)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups. The product is washed with acetonitrile.

A solution of 2% dichloroacetic acid in dichloromethane (volume/volume) is added to deprotect the 5-hydroxyl groups. The product is washed with acetonitrile. A 0.2 M solution of 3-(N-benzoyladenin-9-yl)-4-(4, 4'-dimethoxytrityloxymethyl)-2-azetidinone-1-N-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups. The product is washed with acetonitrile.

A solution of 2% dichloroacetic acid in dichloromethane (volume/volume) is added to deprotect the 5-hydroxyl groups. The product is washed with acetonitrile. A 0.2 M solution of 3-(N-benzoylguanin-9-yl)-4-(4,4'-dimethoxytrityloxymethyl)-2-azetidinone-1-N-O-(2-cyanoethyl N,N-diisopropylphosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5-hydroxyl groups. The product is washed with acetonitrile.

A solution of 2% dichloroacetic acid in dichloeomethane (volume/volume) is added to deprotect the 5-hydroxyl groups. The product is washed with acetonitrile. A 0.2 M solution of N-4-benzoyl-5'-O-(4,4'-dimethoxytrityl)-2'-deoxycytidine-3'-O-(2-cyanoethyl N, N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid in dichloromethane (volume/volume) is added to deprotect the 5'-hydroxyl groups. The product is washed with acetonitrile. A 0.2 M solution of N-6-benzoyl-5'-O-(4,4'-dimethoxytrityl)-2'-deoxyadenosine-3'-O-(2-cyanoethyl N,N- diisopropylphosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

A solution of 2% dichloroacetic acid in dichloromethane (volume/volume) is added to deprotect the 5'-hydroxyl groups. The product is washed with acetonitrile. A 0.2 M solution of N-2-benzoyl-5'-O-(4,4'-dimethoxytrityl)-2'-deoxyguanosine-3'-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl groups. The product is washed with acetonitrile.

The carrier containing the compound is treated with 30% aqueous ammonium hydroxide solution for 2×90 minutes at room temperature. The aqueous solution is filtered and concentrated under reduced pressure to give the phosphorothioate decamer 5'-d(GAC)-bL(GACT)-d(CTT)-3'<SEQ. ID NO 1>.

EXAMPLE 33

1-tert-Butyldimethylsilyloxy-3-hydroxypropane

To a suspension of sodium hydride (0.1 mole) in anhydrous tetrahydrofuran (200 ml) cooled to 0° C. with stirring under an atmosphere of nitrogen is added a solution of 1,3-dihydroxypropane (0.1 mole) in tetrahydrofuran (150 ml) slowly over a period of 1 hour. Then a solution of tert-butyldimethylsilyl chloride (0.1 mole) in tetrahydrofuran (150 ml) is added slowly over a period of 1 hour. Stirring is continued for 6 hours. The mixture is then diluted with ethyl acetate (400 ml), washed with water (100 ml), brine (75 ml), dried and concentrated to afford the title compound.

EXAMPLE 34

3-tert-butyldimethylsilyloxypropionaldehyde

To a solution of anhydrous dimethylsulfoxide (0.05 mole) in anhydrous methylene chloride (100 ml) cooled to 0° C. under nitrogen with stirring is added a solution of oxalyl chloride (0.05 mole) in anhydrous methylene chloride (100 ml). After stirring for 15 minutes, a solution of 1-tert-Butyldimethylsilyloxy-3-hydroxypropane (0.04 mole) in methylene chloride (150 ml) is added over a period of 30 minutes. Then the reaction is quenched by adding triethyl amine (1 mole) slowly. The reaction mixture is diluted with ethyl acetate (200 ml), washed with water (75 ml), brine (75 ml), dried and concentrated. The product is used as such in the subsequent condensation step.

EXAMPLE 35

2-Acetoxy-1-aminoethane

To a stirred solution of 2-aminoethanol (0.1 mole) in tetrahydrofuran (100 ml) is added distilled acetic anhydride (0.1 mole). The reaction mixture is stirred at room temperature for 12 hours and then concentrated to afford the title ocompound.

EXAMPLE 36

Preparation of Imine

2-Acetoxy-1-aminoethane (40 mmole) is dissolved in dichloromethane (150 ml), and a solution of 3-tert-butyldimethylsilyloxypropionaldehyde (40 mmole) in dichloromethane (50 ml) is added slowly under nitrogen at 0° C. The reaction mixture is stirred for 30 minutes and then 4 A molecular sieves (15 g) are added to it. After stirring for 4 hours, the reaction mixture is flitered and concentrated to give the imine.

EXAMPLE 37

N-1-Carboxyethylthymine

To a suspension of thymine (0.317 mole) and potassium carbonate (0.634 mole) in dimethylformamide (900 ml) is added methyl bromopropionate (0.634 mole) and the mixture is stirred vigorously overnight under an atmosphere of nitrogen. The mixture is filtered, washed with ether and evaporated to dryness in vacuo. The solid residue is treated with water (300 ml) and 4 N hydrochloric acid (12 ml), stirred for 20 minutes at 0° C., filtered and washed with water (2×100 ml). The precipitate is treated with water and 2 N sodium hydroxide (60 ml), and is boiled for 10 minutes. The mixture is cooled at 0° C., filtered, and the title compound is precipitated by the addition of 4 N hydrochloric acid (70 ml) to afford, after filtration, the title compound.

EXAMPLE 38

N-4-Benzoyl-N-1-carboxyethylcytosine

To a suspension of N-4-benzoylcytosine (0.317 mole) and potassium carbonate (0.317 mole) in dimethylformamide (900 ml) is added benzyl bromopropionate (0.317 mole) and the mixture is stirred vigorously overnight under nitrogen. The mixture is filtered, washed with ether and evaporated to dryness, in vacuo. The solid residue is dissolved in methanol (50 ml) and hydrogenated using Raney nickel (5 g) under 40 psi pressure of hydrogen for 6 hours. The reaction mixture is filtered, the catalyst washed with methanol (20 ml) and the combined fractions are concentrated to afford the title compound.

EXAMPLE 39

N-9-Carboxyethyladenine Benzyl Ester

Adenine (74 mmole) and potassium carbonate (74 mmole) are suspended in DMF (100 ml) and benzyl bromopropionate (74 mmole) in DMF (20 ml) is added. The suspension is stirred for 3 hours under nitrogen at room temperature, and then filtered. The solid residue is washed three times with DMF (25 ml), and the combined filtrate is evaporated to dryness, in vacuo, to give the title compound.

EXAMPLE 40

N-6-Benzoyl-N-9-carboxyethyladenine Benzyl Ester

To a stirred solution of N-9-carboxyethyladenine benzyl ester (15 mmole) and pyridine (25 ml) in DMF (50 ml) is added a solution of benzoic anhydride (60 mmole) in DMF (30 ml) with ice-cooling. The ice-bath is removed and the mixture is stirred overnight. The reaction mixture is concentrated to afford the title compound.

EXAMPLE 41

N-6-Benzoyl-N-9-carboxyethyladenine

N-6-benzoyl-N-9-carboxyethyladenine benzyl ester (10 mmole) is taken up in methanol (50 ml) and hydrogenated using Raney nickel (5 g) under 40 psi pressure of hydrogen for 6 hours. The reaction mixture is filtered, the catalyst washed with methanol (20 ml) and the combined fractions are concentrated to afford the title compound.

EXAMPLE 42

N-9-Carboxethylguanine Benzyl Ester

Guanine (74 mmole) and potassium carbonate (74 mmole) are suspended in DMF (100 ml) and benzyl bromopropionate (74 mmole) in DMF (20 ml) is added. The suspension is stirred for 3 hours under nitrogen at room temperature, and then filtered. The solid residue is washed three times with DMF (25 ml), and the combined filtrate is evaporated to dryness, in vacuo.

EXAMPLE 43

N-2-Benzoyl-N-9-carboxyethylguanine Benzyl Ester

To a stirred solution of N-9-carboxyethyladenine benzyl ester (15 mmole) and pyridine (25 ml) in DMF (50 ml) is added a solution of benzoic anhydride (60 mmole) in DMF (30 ml) with ice-cooling. The ice-bath is removed and stirred overnight. The reaction mixture is concentrated to afford the title compound.

EXAMPLE 44

N-2-Benzoyl-N-9-carboxyethylguanine

N-2-Benzoyl-N-9-carboxyethyladenine benzyl ester (10 mmole) is taken up in methanol (50 ml) and hydrogenated using Raney nickel (5 g) under 40 psi pressure of hydrogen for 6 hours. The reaction mixture is filtered, the catalyst washed with methanol (20 ml) and the combined fractions are concentrated to afford the title compound.

EXAMPLE 45

1-N-(2-acetoxy)ethyl-3-(thymidin-1-yl)methyl-4-(2-tert-butyldimethylsilyloxy)ethyl-2-azetidinone To a stirred suspension of N-1-carboxyethylthymine (20 mmole) in DMF (50 ml) is added 2-chloro-1-methylpyridiniumiodide (20 mmole) and heated gently until the solution becomes homogenous. The reaction mixture is slowly cooled to room temperature and then a solution of imine, prepared using the procedure of Example 36, by the condensation of 3-tert-butyldimethylsilyloxypropionaldehyde and 2-acetoxy-1-aminoethane (20 mmole), in DMF (20 ml) is added slowly over a period of 20 minutes. The reaction mixture is stirred overnight and concentrated under reduced pressure. The crude product is purified by flash chromatography over silica gel to give the title compound.

EXAMPLE 46

1-N-(2-Acetoxy)ethyl-3-(4-N-benzoylcytosin-1-yl)methyl-4-(2-tert-butyldimethylsilyloxy)ethyl-2-azetidinone To a stirred suspension of N-4-benzoyl-N-1-carboxyethylcytosine (20 mmole) in DMF (50 ml) is added 2-chloro-1-methylpyridiniumiodide (20 mmole) and heated gently until the solution becomes homogenous. The reaction mixture is slowly cooled to room temperature and then a solution of imine, prepared using the procedure of Example 36, by the condensation of 3-tert-butyldimethylsilyloxypropionaldehyde and 2-acetoxy-1-aminoethane (20 mmole) in DMF (20 ml) is added slowly over a period of 20 minutes. The reaction mixture is stirred overnight and concentrated under reduced pressure. The crude material is purified by flash chromatography over silica gel to give the title compound.

EXAMPLE 47

1-N-(2-acetoxy)ethyl-3-(6-N-benzoyladenin-1-yl)-methyl-4-(2-tert-butyldimethylsilyloxy)ethyl-2-azetidinone To a stirred suspension of N-6-benzoyl-N-1-carboxyethyladenine (20 mmole) in DMF (50 ml) is added 2-chloro-1-methylpyridiniumiodide (20 mmole) and the mixture is heated gently until the solution becomes homogenous. The reaction mixture is slowly cooled to room temperature and then a solution of imine, prepared using the procedure of Example 36, by the condensation of 3-tert-butyldimethylsilyloxy propionaldehyde and 2-acetoxy-1-aminoethane (20 mmole) in DMF (20 ml) is added slowly over a period of 20 minutes. The reaction mixture is stirred overnight and concentrated under reduced pressure. The crude material is purified by flash chromatography over silica gel to give the title compound.

EXAMPLE 48

1-N-(2-acetoxy)ethyl-3-(2-N-benzoylguanin-9-yl)-methyl-4-(2-tert-butyldimethylsilyloxy)ethyl-2-azetidinone To a stirred suspension of N-2-benzoyl-N-1-carboxyethylguanine (20 mmole) in DMF (50 ml) is added 2-chloro-1-methylpyridiniumiodide (20 mmole) and the mixture is heated gently until the solution becomes homogenous. The reaction mixture is slowly cooled to room temperature and then a solution of imine, prepared using the procedure of Example 36, by the condensation of 3-tert-butyldimethylsilyloxy propionaldehyde and 2-acetoxy-1-aminoethane (20 mmole) in DMF (20 ml) is added slowly over a period of 20 minutes. The reaction mixture is stirred overnight and concentrated under vacuo. The crude product is purified by flash chromatography over silica gel to afford the product as a crystalline solid.

EXAMPLE 49

1-N-(2-acetoxy)ethyl-3-(thymidin-1-yl)methyl-4-hydroxy-ethyl-2-azetidinone

1-N-(2-Acetoxy)ethyl-3-(thymidin-1-yl)methyl-4-(-2-tert-butyldimethylsilyloxy)ethyl-2-azetidinone (prepared as per the procedure of Example 46), (10 mmole) is taken up in tetrahydrofuran (50 ml) and tetrabutylammonium fluoride (25 mmole) is added at room temperature and stirred for 2 hours. The reaction mixture is filtered,and concentrated to give the title compound.

EXAMPLE 50

1-N-(2-acetoxy)ethyl-3-(4-N-benzoylcytosin-1-yl)methyl-4-hydroxyethyl-2-azetidinone 1-N-(2-Acetoxy) ethyl-3-(4-N-benzoylcytosinyl)methyl-4-(-2-tert-butyldimethylsilyloxy)ethyl-2-azetidinone (10

EXAMPLE 51

1-N-(2-acetoxy)ethyl-3-(6-N-benzoyladenin-1-yl) methyl-4-hydroxyethyl-2-azetidinone 1-N-(2-acetoxy)ethyl-3-(6-N-benzoyladenin-1-yl) methyl-4-(2-tert-butyldimethylsilyloxy)ethyl-2-azetidinone (10 mmole) is taken up in tetrahydrofuran (50 ml) and tetrabutylammonium fluoride (25 mmole) is added at room temperature and stirred for 2 hours. The reaction mixture is filtered and concentrated to give the title compound.

EXAMPLE 52

1-N-(2-Acetoxy)ethyl-3-(2-N-benzoylguanin-1-yl) methyl-4-hydroxyethyl-2-azetidinone 1-N-(2-acetoxy)ethyl-3-(2-N-benzoylguanin-1-yl) methyl-4-(2-tert-butyldimethylsilyloxy)ethyl-2-azetidinone (10 mmole) is taken up in tetrahydrofurane (50 ml) and tetrabutylammonium fluoride (25 mmole) is added at room temperature and stirred for 2 hours. The reaction mixture is filtered and concentrated to give the title compound.

EXAMPLE 53

1-N-(2-Acetoxy)ethyl-3-thymidin-1-ylmethyl-4-dimethoxytrityl-oxyethyl-2-azetidinone 1-N-(2-acetoxy)ethyl-3-(thymidin-1-yl)methyl-4-hydroxy-ethyl-2-azetidinone (10 mmole) is taken up in dichloromethane (50 ml) and dimethoxytrityl chloride (25 mmole) and pyridine (50 mmole) are added at room temperature. The mixture is stirred for 12 hours. The reaction mixture is filtered and concentrated. The crude material is purified by silica gel flash column chromatography to give the title compound.

EXAMPLE 54

1-N-(2-Acetoxy)ethyl-3-(4-N-benzoylcytosin-1-yl) methyl-4-dimethoxytrityloxyethyl-2-azetidinone 1-N-(2-acetoxy)ethyl-3-(4-N-benzoylcytosin-1-yl) methyl-4-hydroxyethyl-2-azetidinone (10 mmole) is taken up in dichloromethane (50 ml) and dimethoxytrityl chloride (25 mmole) and pyridine (50 mmole) are added at room temperature and stirred for 12 hours. The reaction mixture is filtered and concentrated. The crude material is purified by silica gel flash column chromatography to give the title compound.

EXAMPLE 55

1-N-(2-Acetoxy)ethyl-3-(6-N-benzoyladenin-1-yl) methyl-4-dimethoxytrityloxyethyl-2-azetidinone 1-N-(2-acetoxy)ethyl-3-(6-N-benzoyladenin-1-yl) methyl- 4-hydroxyethyl-2-azetidinone (10 mmole) is taken up in dichloro-methane (50 ml) and dimethoxytrityl chloride (25 mmole) and pyridine (50 mmole) are added at room temperature and stirred for 12 hours. The reaction mixture is filtered and concentrated. The crude material is purified by silica gel flash column chromatography to give the title compound.

EXAMPLE 56

1-N-(2-Acetoxy)ethyl-3-(2-N-benzoylguanin-1-yl) methyl-4-dimethoxytrityloxyethyl-2-azetidinone 1-N-(2-acetoxy)ethyl-3-(2-N-benzoylguanin-1-yl) methyl-4-hydroxyethyl-2-azetidinone (10 mmole) is taken up in dichloromethane (50 ml) and dimethoxytrityl chloride (25 mmole) and pyridine (50 mmole) are added at room temperature and stirred for 12 hours. The reaction mixture is filtered and concentrated. The crude material is purified by silica gel flash column chromatography to give the title compound.

EXAMPLE 57

1-N-2-Hydroxyethyl-3-(thymidin-1-yl)methyl-4-dimethoxytrityloxyethyl-2-azetidinone 1-N-(2-Acetoxy)ethyl-3-(thymidin-1-yl)methyl-4-hydroxyethyl-2-azetidinone (10 mmole) is taken up in methanol (50 ml) and potassium cyanide (15 mmole) is added at room temperature and stirred for 12 hours. The reaction mixture is filtered and concentrated. The crude material is purified by silica gel flash column chromatography to give the title compound.

EXAMPLE 58

1-N-2-Hydroxyethyl-3-(4-N-benzoylcytosin-1-yl) methyl-4-dimethoxytrityloxyethyl-2-azetidinone 1-N-(2-Acetoxy)ethyl-3-(4-N-benzoylcytosin-1-yl) methyl-4-hydroxyethyl-2-azetidinone (10 mmole) is taken up in methanol (50 ml) and potassium cyanide (15 mmole) is added at room temperature and the mixture is stirred for 12 hours. The reaction mixture is filtered and concentrated. The crude material is purified by silica gel flash column chromatography to give the title compound.

EXAMPLE 59

1-N-2-Hydroxyethyl-3-(6-N-benzoyladenin-1-yl) methyl-4-dimethoxytrityloxyethyl-2-azetidinone 1-N-(2-Acetoxy) ethyl-3-(6-N-benzoyladenin-1-yl) methyl-4-hydroxyethyl-2-azetidinone (10 mmole) is taken up in methanol (50 ml) and potassium cyanide (15 mmole) is added at room temperature and stirred for 12 hours. The reaction mixture is filtered and concentrated. The crude material is purified by silica gel flash column chromatography to give the title compound.

EXAMPLE 60

1-N-2-Hydroxyethyl-3-(2-N-benzoylguanin-1-yl) methyl-4-dimethoxytrityloxyethyl-2-azetidinone 1-N-(2-Acetoxy)ethyl-3-(2-N-benzoylguaninyl)methyl-4-hydroxyethyl-2-azetidinone (10 mmole) is taken up in methanol (50 ml) and potassium cyanide (15 mmole) is added at room temperature and the mixture is stirred for 12 hours. The reaction mixture is filtered and concentrated. The crude material is purified by silica gel flash column chromatography to give the title compound.

EXAMPLE 61

3-(Thymidin-1-yl)methyl-4-dimethoxytrityloxyethyl-2-azetidin-one-1-N-ethyl-O-(2-cyanoethylN,N-diisopropylphosphoroamidite)

To a solution of 1-N-2-hydroxyethyl-3-(thymidin-1-yl) methyl-4-dimethoxytrityloxyethyl-2-azetidinone (12mmole) in acetonitrile (30 ml) is added diisopropylammonium tetrazolide (12 mmole) followed by 2-cyanoethyl bis[N,N-diisopropyl]-phosphoramidite (18 mmole) in acetonitrile (20 ml). The reaction mixture is stirred under an atmosphere of argon at room temperature for 2 hours. The reaction mixture is diluted with ethylacetate (75 ml), washed with dilute sodium hydrogen carbonate (20 ml) and then brine. The ethyl acetate layer is dried and concentrated under reduced pressure. The crude product is purified by silica gel flash column chromatography using ethyl acetate/ dichloromethane as eluants to give the title compound.

EXAMPLE 62

3-(4-N-Benzoylcytosin-1-yl)methyl-4-dimethoxytrityloxyethyl-2-azetidinone-1-N-ethyl-O-(2-cyanoethyl N,N-diisopropylphosphoramidite)

To a solution of 1-N-2-hydroxyethyl-3-(4-N-benzoylcytosin-1-yl)methyl-4-dimethoxytrityloxyethyl-2-azetidinone (12 mole) in acetonitrile (30 ml) is added diisopropylammonium tetrazolide (12 mmole) followed by 2-cyanoethyl bis[N,N-diisopropyl]phosphoroamidite (18 mmole) in acetonitrile (20 ml). The reaction mixture is stirred under an atmosphere of argon at room temperature for 2 hours. The reaction mixture is diluted with ethylacetate (75 ml), washed with dilute sodium hydrogen carbonate (20 ml) and then brine. The ethyl acetate layer is dried and concentrated under reduced pressure. The crude product is purified by silica gel flash column chromatography using ethyl acetate/dichloromethane as eluants to give the title compound.

EXAMPLE 63

3-(6-N-Benzoyladenin-1-yl)methyl-4-dimethoxytrityloxyethyl-2-azetidinone-1-N-ethyl-O-(2-cyanoethyl N,N-diisopropylphosphoroamidite)

To a solution of 1-N-2-hydroxyethyl-3-(6-N-benzoyladenin-1-yl)methyl-4-dimethoxytrityloxyethyl-2-azetidinone (12 mmole) in acetonitrile (30 ml) is added diisopropylammonium tetrazolide (12 mmole) followed by 2-cyanoethyl bis[N,N-diisopropyl]phosphoramidite (18 mmole) in acetonitrile (20 ml). The reaction mixture is stirred under an atmosphere of argon at room temperature for 2 hours. The reaction mixture is diluted with ethylacetate (75 ml), washed with dilute sodium hydrogen carbonate (20 ml) and then brine. The ethyl acetate layer is dried and concentrated under reduced pressure. The crude product is purified by silica gel flash column chromatography using ethyl acetate/dichloromethane as eluants to give the title compound.

EXAMPLE 64

3-(2-N-Benzoylguanin-1-yl)methyl-4-dimethoxytrityloxyethyl-2-azetidinone-1-N-ethyl-O-(2-cyanoethyl N,N-diisopropylphosphoramidite)

To a solution of 1-N-2-hydroxyethyl-3-(2-N-benzoylguanin-1-yl)methyl-4-dimethoxytrityloxyethyl-2-azetidinone (12 mmole) in acetonitrile (30 ml) is added diisopropylammonium tetrazolide (12 mmole) followed by 2-cyanoethyl bis [N,N-diisopropyl]phosphoramidite (18 mmole) in acetonitrile (20 ml). The reaction mixture is stirred under an atmosphere of argon at room temperature for 2 hours. The reaction mixture is diluted with ethylacetate (75 ml), washed with dilute sodium hydrogen carbonate (20 ml) and then brine. The ethyl acetate layer is dried and concentrated under reduced pressure. The crude product is purified by silica gel flash column chromatography using ethyl acetate/dichloromethane as eluants to give the title compound.

EXAMPLE 65

Synthesis of bL(GACT) Phosphorothioate Tetramer

1-N-Hydroxyethyl-3-(thymidin-1-yl)methyl-4-(dimethoxytrityloxyethyl-2-azetidinone (2 mmole) bonded to CPG (controlled pore glass) through an ester linkage is transferred to a glass reactor, and a dichloromethane solution of 2% dichloroacetic acid (volume/volume) is added to deprotect the 4-ethyl hydroxyl group. The solid support and bound material is washed with acetonitrile. A 0.2 M solution of 3-(4-N-benzoylcytosin-1-yl)methyl-4-dimethoxytrityloxyethyl-2-azetidinone-1-N-ethyl-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

A dichloromethane solution of 2% dichloroacetic acid (volume/volume) is added to deprotect the 4-ethyl hydroxyl group. The product is washed with acetonitrile. A 0.2 M solution of 3-(6-N-benzoyladenin-1-yl)methyl-4-dimethoxytrityloxyethyl-2-azetidinone-1-N-ethyl-O-(2-cyanoethyl N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

A dichloromethane solution of 2% dichloroacetic acid (volume/volume) is added to deprotect the 4-ethyl hydroxyl group. The product is washed with acetonitrile. A 0.2 M solution of 3-(2-N-benzoylguanin-1-yl)methyl-4-dimethoxytrityloxyethyl-2-azetidinone-1-N-ethyl-o-(2-cyanoethyl N,N-diisopropyl phosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

The carrier containing the compound is treated twice with 30% ammonium hydroxide solution for 90 minutes at room temperature. The aqueous solution is filtered and concentrated under reduced pressure to give the phosphorothioate tetramer bL(GACT).

EXAMPLE 66

Synthesis of bL(GACT) Phosphodiester Tetramer

1-N-Hydroxyethyl-3-(thymidin-1-yl)methyl-4-dimethoxytrityloxyethyl-2-azetidinone (2 mmole) bonded to CPG (controlled pore glass) through an ester linkage is transferred to a glass reactor and a dichloromethane solution of 2% dichloroacetic acid (volume/volume) is added to deprotect the 4-ethyl hydroxyl group. The product is washed with acetonitrile. A 0.2 M solution of 3-(4-N-benzoylcytosin-1-yl)methyl-4-dimethoxytrityloxy ethyl-2-azetidinone-1-N-ethyl-O-(2-cyanoethyl N,N-diisopropyl phosphoramidite) in acetonitrile and a 0.4 M solution of 1H-tetrazole in acetonitrile is added and reacted at room temperature for 5 minutes. The product is washed with acetonitrile, and then a 0.05 M solution of tert-butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

A dichloromethane solution of 2% dichloroacetic acid (volume/volume) is added to deprotect the 4-ethyl hydroxyl group. The product is washed with acetonitrile. A 0.2 M solution of 3-(6-N-benzoyladenin-1-yl)methyl-4-dimethoxytrityloxyethyl-2-azetidinone-1-N-ethyl-O-(2-cyanoethyl N,N-diisopropyl phosphoramidite) in acetonitrile and a 0.4 M solution of 1H-tetrazole in acetonitrile is added and reacted at room temperature for 5 minutes. The product is washed with acetonitrile, and then a 0.05 M solution of tert-butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

A dichloromethane solution of 2% dichloroacetic acid (volume/volume) is added to deprotect the 4-ethyl hydroxyl group. The product is washed with acetonitrile. Then, a 0.2 M solution of 3-(2-N-benzoylguanin-1-yl)methyl-4-dimethoxytrityloxyethyl-2-azetidinone-1-N-ethyl-O-(2-cyanoethyl N,N-diisopropyl phosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of tert-butyl hydroperoxide in acetonitrile is added and reacted at room temperature for 5 minutes. This oxidation step is repeated one more time for 5 minutes. The support is washed with acetonitrile and then a solution of acetic anhydride/lutidine/THF (1:1:8), and N-methyl imidazole/THF is added to cap any unreacted 4-ethyl hydroxyl groups. The product is washed with acetonitrile.

The carrier containing the compound is treated twice with a 30% ammonium hydroxide solution for 90 minutes at room temperature. The aqueous solution is filtered and concentrated under reduced pressure to give the phosphorothioate tetramer bL(GACT).

---

---

What is claimed is:

1. A method for preparing a β-lactamtide comprising:
   a) providing a β-lactam having a functional group, a protected hydroxyl group, and a hydroxyl group covalently bonded thereto;
   said functional group is a nucleobase, furthermore, said functional group can be optionally substituted with one or more additional functional groups selected from hydrogen, hydroxyl, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, or a reporter ligand;
   b) attaching said β-lactam to a solid support via said hydroxyl group;
   c) treating said protected hydroxyl group with a deprotecting reagent to give a free hydroxyl group;
   d) reacting said free hydroxyl group with a β-lactamtide having an activated phosphite group, a functional group as defined above, and a protected hydroxyl group thereon to form a phosphite triester;
   e) oxidizing said phosphite triester to a phosphate triester or to a phosphorothioate;
   wherein said functional group attached to said β-lactam and said functional group attached to said β-lactamtide are each optionally attached using a tether of formula $(CR_6R_7)_x$ where $R_6$ and $R_7$ are independently selected from the group consisting of hydrogen. $(C_2-C_6)$alkyl aryl, aralkyl, heteroaryl hydroxy, $(C_1-C_6)$alkoxvy $(C_1-C_6)$alkylthio, $NR_3R_4$ and $SR_5$, where each of $R_3$ and $R_4$ is independently selected from the group consisting of hydrogen, $(C_1-C_4)$alkyl, alkoxy, or alkylthio-substituted $(C_1-C_4)$ alkyl, alkoxy, alkylthio and amino; and $R_5$ is hydrogen, $(C_1-C_6)$alkyl hydroxy-, alkoxy-, or alkylthio- substituted ($C_1$–$C_6$)alkyl, or $R_6$ and $R_7$ taken together complete an alicyclic system, and where $x$ is an integer from 1 to 10, and can be 0 only when said functional group is not hydrogen or hydroxyl.

2. The method of claim 1 wherein steps c, d, and e are repeated iteratively to give a predetermined number of β-lactamtides in the final composition.

3. The method of claim 1 wherein said functional group attached to said β-lactam and said functional group attached to said β-lactamtide is attached using a tether.

4. The method of claim 1 wherein said hydroxyl group and said protected hydroxyl group are independently attached to said β-lactam and said protected hydroxyl group and said activated phosphite group are independently attached to said β-lactamtide using an alkyl tether, wherein said alkyl tether is a $C_1$ to about $C_6$ alkyl tether.

5. The method of claim 4 wherein said alkyl tether is a $C_1$ to $C_3$ alkyl tether.

6. The method of claim 1 wherein said hydroxyl group is covalently bonded to said β-lactam at the N-1 position.

7. The method of claim 6 further including a $C_1$–$C_3$ alkyl tether between said hydroxyl group and said N-1 position.

8. The method of claim 1 wherein said protected hydroxyl group is covalently bonded to the C-4 position of said β-lactam and said protected hydroxyl group is covalently bonded to the C-4 position of said β-lactamtide.

9. The method of claim 8 further including a $C_1$–$C_3$ alkyl tether between said protected hydroxyl group and the N-1 position of said β-lactam.

10. The method of claim 1 wherein said activated phosphite group is covalently bonded to the N-1 position of said β-lactamtide.

11. The method of claim 1 wherein said hydroxyl group is covalently bonded to the N-1 position of said β-lactam, and said β-lactam is formed by treatment of a fully protected dihydroxy substituted β-lactam with a weak base to selectively cleave the protecting group from said hydroxyl group covalently bonded to the N-1 position of said β-lactam.

12. The method of claim 1 wherein said phosphite triester is treated with a capping reagent.

13. The method of claim 1 wherein said phosphite triester is oxidized to a phosphorothioate.

14. The method of claim 1 wherein the functional group is a naturally occurring nucleobase.

* * * * *

UNITED STATES PATENT AND TRADEMARK OFFICE
CERTIFICATE OF CORRECTION

PATENT NO. : 6,084,082
DATED : July 4, 2000
INVENTOR(S) : Ravikumar et al.

It is certified that error appears in the above-identified patent and that said Letters Patent is hereby corrected as shown below:

Column 11,
Line 1, please delete "βlactamide" and insert therefor -- β-lactamide --;
Line 65, please delete "βlactam" and insert therefor -- β-lactam --;

Column 13,
Line 39, please delete "βlactam" and insert therefor -- β-lactam --;

Column 19,
Lines 45 and 63, please delete "dimethoxytrityloxymethy" and insert therefor -- dimethoxytrityloxymethyl --;

Column 23,
Line 1, please delete the "10" after "4,4'-";
Line 23, please delete "30" after "N,N-diisopropyl-";

Column 26,
Line 3, please delete "ocompound" and insert therefor -- compound --

Column 29,
Line 31, please delete "ylmethyl" and insert therefor -- yl) methyl --;

Column 30,
Line 53, please delete "(2-N-benzoylguaninyl" and insert therefor -- (2-N-benzoylguanin-1-yl) --;

Column 32,
Line 51, please delete "o" and insert therefor -- O --;

UNITED STATES PATENT AND TRADEMARK OFFICE
CERTIFICATE OF CORRECTION

PATENT NO.   : 6,084,082
DATED        : July 4, 2000
INVENTOR(S)  : Ravikumar et al.

It is certified that error appears in the above-identified patent and that said Letters Patent is hereby corrected as shown below:

Column 34,
Line 62, please delete "alkoxvy" and insert therefor -- alkoxy --.

Signed and Sealed this

Fifth Day of March, 2002

Attest:

JAMES E. ROGAN
Attesting Officer    Director of the United States Patent and Trademark Office

SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Novel Sequence

<400> SEQUENCE: 1
gacgactctt                                                            10